(12) United States Patent
Merlin

(10) Patent No.: US 8,570,228 B2
(45) Date of Patent: Oct. 29, 2013

(54) PATIENT DEVICE HAVING AN ANTENNA ARRAY WITH POLARIZATION DIVERSITY

(75) Inventor: Julian Merlin, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 817 days.

(21) Appl. No.: 12/480,950

(22) Filed: Jun. 9, 2009

(65) Prior Publication Data

US 2009/0315790 A1 Dec. 24, 2009

(30) Foreign Application Priority Data

Jun. 23, 2008 (DE) .......................... 10 2008 002 587

(51) Int. Cl.
*H01Q 21/00* (2006.01)
*H01Q 7/00* (2006.01)
*H01Q 9/16* (2006.01)

(52) U.S. Cl.
USPC ............ 343/726; 343/718; 343/747; 343/748

(58) Field of Classification Search
USPC ......... 343/726, 745, 747, 748, 846, 725, 727, 343/728
See application file for complete search history.

(56) References Cited

U.S. PATENT DOCUMENTS

| | | | |
|---|---|---|---|
| 2,465,379 A * | 3/1949 | Kandoian | 343/726 |
| 5,751,252 A | 5/1998 | Phillips | |
| 6,070,803 A * | 6/2000 | Stobbe | 235/492 |

FOREIGN PATENT DOCUMENTS

| | | |
|---|---|---|
| DE | 60030733 | 9/2006 |
| EP | 1 339 131 | 8/2003 |
| EP | 1 655 850 | 5/2006 |
| EP | 1643592 | 7/2008 |
| JP | 2001 332930 | 11/2001 |
| JP | 2001332930 A * | 11/2001 |
| WO | WO 2005/115541 | 12/2005 |
| WO | WO 2005123186 | 12/2005 |

OTHER PUBLICATIONS

European Search Report, Oct. 14, 2009, 3 pages.
Krischke: "Rothammels Antennenbuch" 2002, Darc Verlag, Baunatal, pp. 206-207.
German Search Report, dated May 27, 2009.

* cited by examiner

*Primary Examiner* — Robert Karacsony
(74) *Attorney, Agent, or Firm* — ARC IP Law, PC; Joseph J. Mayo

(57) ABSTRACT

A patient device that possesses a receiver array having particularly great reception sensitivity. The patient device possesses an E-field antenna and an H-field antenna, in each instance, where the H-field antenna is structured as a frame antenna. According to the invention, a main axis that runs through the E-field antenna forms an angle of less than 30 degrees to a normal line of an area generated by the frame antenna.

11 Claims, 6 Drawing Sheets

PATIENT DEVICE HAVING AN ANTENNA ARRAY WITH POLARIZATION DIVERSITY

This application takes priority from German Patent Application DE 10 2008 002 587.9, filed 23 Jun. 2008, the specification of which is hereby incorporated herein by reference.

BACKGROUND OF THE INVENTION

1. Field of the Invention

The invention relates to a patient device having an antenna array with polarization diversity.

2. Description of the Related Art

In the medical technology sector, what are called patient devices are increasingly being used, which can be carried along by the patient and usually receive medical or technical data from an implant, such as a heart pacemaker of a patient, for example, at regular intervals, by way of a wireless data connection, and keep these data available for monitoring by the physician, or transmit them directly to a suitable device, for medical monitoring. Since electro-medical implants can only be replaced by means of an operation, and therefore are supposed to remain in the patient's body for multiple years, operated by a battery, the additional power consumption to be expended for such a telemetry function represents a critical factor in implementation. In order to minimize the transmission power to be expended for reliable data transmission, a particularly sensitive reception array in the patient device is desirable. The present invention therefore has the task of indicating a patient device that possesses a reception array having particularly great reception sensitivity.

BRIEF SUMMARY OF THE INVENTION

In order to meet the above-stated requirements, the invention indicates a patient device that has a transmitter/receiver device having an E-field antenna and a H-field antenna, in each instance, where the H-field antenna is configured as a frame antenna. According to the invention, a main axis that runs through the E-field antenna forms an angle of less than 30 degrees relative to the normal line of an area generated by the frame antenna.

This geometric arrangement possesses the advantage that the E-field antenna and the H-field antenna cannot reciprocally influence one another. In this connection, "main axis" is understood to mean the axis that extends for the greatest possible distance within the E-field antenna.

The least influence of E-field antenna and H-field antenna results if the main axis is approximately parallel, or, even better, precisely parallel to the normal line.

In the case of an embodiment variant that is preferred because of its particularly compact construction, the main axis runs through the generated area. Particularly preferably, the main axis runs through an area center of gravity of the generated area.

Preferably, the E-field antenna and/or the H-field antenna is/are electrically extended. This can be brought about, in the case of the E-field antenna, in known manner, for example by means of a coil at the feed point of the antenna, or by means of a capacitor attached to the tip of the E-field antenna; in the case of the H-field antenna, it can be brought about by means of providing multiple loop windings.

The E-field antenna can be structured as a rod antenna or as a helical antenna.

Particularly preferably, the E-field antenna and the H-field antenna have a resonance frequency between 300 MHz and 500 MHz. This frequency range is particularly suitable for the transmission of data from medical technology implants.

A particularly preferred embodiment of the patient device according to the invention possesses an antenna array having a particularly robust mechanical structure. In this connection, the E-field antenna is structured as a quarter-wave dipole having an antenna counterweight. In antenna technology, a "counterweight" is a metallic device connected with ground, which can be structured as a plate or star, and reflects the quarter-wave dipole, so that its emission behavior at least approximately corresponds to that of a half-wave dipole. In the preferred embodiment, the antenna counterweight serves, at the same time, to mechanically stabilize the H-field antenna, which is structured as a frame antenna, in that it is connected with the latter (in electrically insulated manner) at least at one point of the H-field antenna.

Particularly preferably, the transmitter/receiver device of the patient device is configured to select either the E-field antenna or the H-field antenna for reception during operation, in each instance, as a function of the reception strength of a received signal. Alternatively, however, it is also possible to sum up the signals of the two antennas.

At least one antenna, the E-field antenna or the H-field antenna, can have an adaptation network that can be tuned by a controller. This makes it possible to maximize the reception or transmission power, respectively, in that during operation, the adaptation of the E-field antenna and/or the H-field antenna can be corrected in accordance with the general conditions predetermined by the environment.

The tunable adaptation network can have a plurality of capacitors that can be switched in parallel, where the controller is configured to connect a partial amount (lying between none and all) of the capacitors with at least one of the E-field antenna and the H-field antenna, and to electrically insulate the remaining capacitors from at least one of the E-field antenna and the H-field antenna.

Alternatively or in addition, for example as "fine-tuning," the tunable adaptation network can contain a varactor diode. The controller is configured to predetermine a cut-off voltage of the varactor diode by way of an inductance. The capacitance of the varactor diode can be adjusted in step-free manner by means of the cut-off voltage. The inductance serves to uncouple the high-frequency antenna signal from the control voltage of the controller.

The E-field antenna and/or the H-field antenna can be connected with the transmitter/receiver device by way of a directional coupler. The directional coupler is configured to output a measurement signal to the controller. In this connection, the measurement signal indicates a measure of the power reflected or received by the E-field antenna and/or the H-field antenna. The measurement signal advantageously allows establishment of a regulation loop for adjusting the tunable adaptation network.

DETAILED DESCRIPTION OF THE INVENTION

Figure 1:
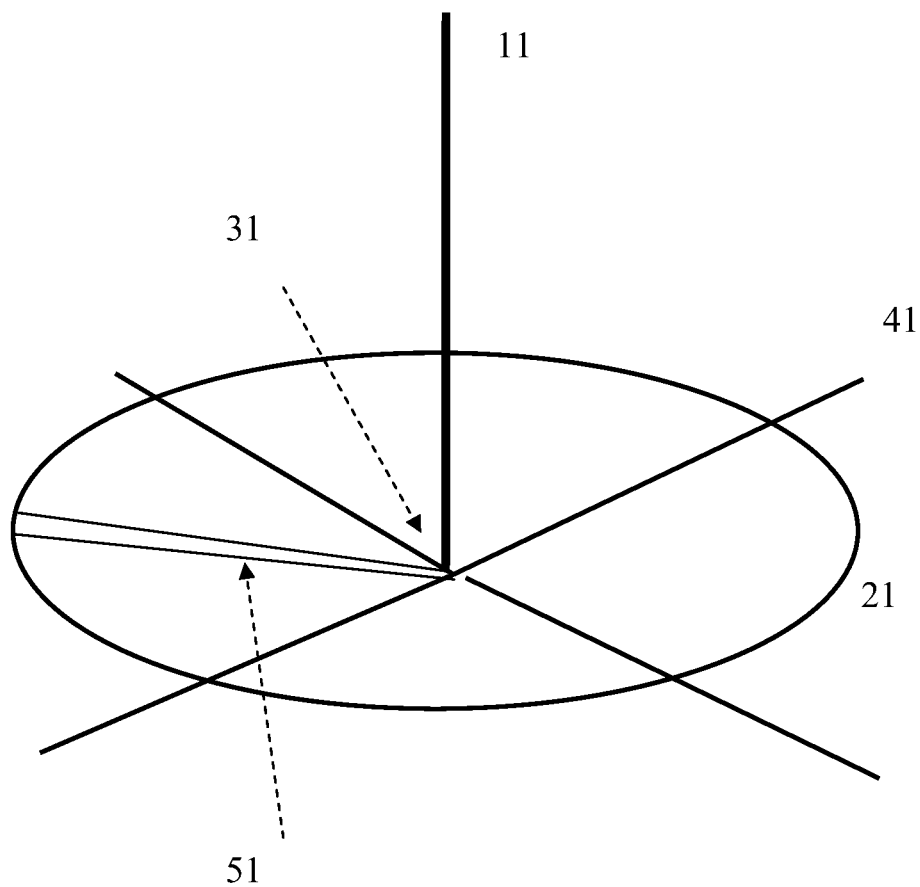
FIG. 1 the antenna array of a first exemplary embodiment of the patient device according to the invention.

FIG. 1 shows the antenna array of a first exemplary embodiment of the patient device according to the invention. An E-field antenna 11, which is preferably structured as an electrically lengthened quarter-wave or helical antenna, is disposed in the center of a circular frame antenna 21, in such a manner that the feed point 31 of the E-field antenna is positioned in the center of the frame antenna 21. The frame antenna 21 can generally be structured also as a loop antenna, which then has two or more spirals. Of course, the frame antenna 21 can also assume other geometrical shapes, such as rectangular, square, triangular, or hexagonal. An antenna counterweight 41 is configured as a right-angle cross of two rigid metallic conductors, the intersection point of which is situated as close as possible to the feed point 31 of the E-field antenna 11, on the side facing away from the E-field antenna 11. The metallic conductors are electrically connected with the ground line to the feed point 31, and are dimensioned in such a manner that they mechanically support the frame antenna 21, from which they are electrically insulated. The antenna counterweight 41 can also be configured as a star of metallic conductors or as a continuous surface, for example. The frame antenna 21 is supplied by way of a feed line 51, which contains a ground-shielded signal line. Preferably, the frame antenna 21 is structured in such a flat manner that the area it covers lies at least approximately in one plane. The frame antenna 21 is disposed relative to the E-field antenna 11 in such a manner that a main axis of the E-field antenna is at least approximately parallel to an area normal line of the area covered by the frame antenna 21. On the basis of this arrangement, the result is achieved that the two antennas do not negatively influence one another. In this connection, "at least approximately parallel" means an angle of less than 30 degrees, but even better, less than 10 degrees. The effect striven for with the geometric arrangement is best if the main axis of the E-field antenna is oriented as parallel as possible to the normal line of the area covered by the H-field antenna, within the usual production tolerances.

Figure 2:
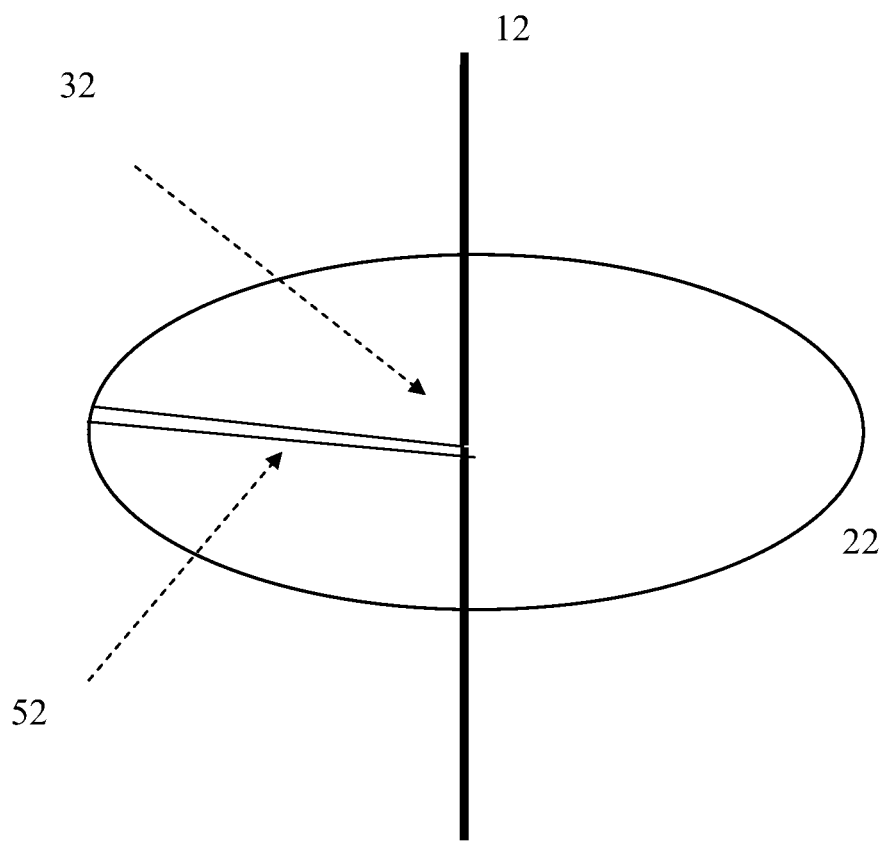
FIG. 2 the antenna array of a second exemplary embodiment of the patient device according to the invention.

FIG. 2 shows the antenna array of a second exemplary embodiment of the patient device according to the invention. In the case of this exemplary embodiment, the E-field antenna 12 is configured as a half-wave dipole, and for this reason, the feed point 32 is situated in the middle of the E-field antenna 12. As a half-wave dipole, the E-field antenna 12 does not have an antenna counterweight. A mechanical connection of the E-field antenna 12 with the frame antenna 22 is therefore preferably made by means of non-conductive materials. Again, the frame antenna 22 is configured to be circular. The E-field antenna 12 is disposed relative to the frame antenna 22 in such a manner that the feed point 32 comes to lie at least approximately at the center point of the area covered by the frame antenna 22. Again, the main axis of the E-field antenna 22 is at least approximately parallel to a normal line of the area covered by the frame antenna 22. The statements made above concerning alternative shapes of the frame antenna 22 apply for this exemplary embodiment, as well. The feed line 52 connects the feed point 32 of the E-field antenna 12 with the frame antenna 22.

Figure 3:
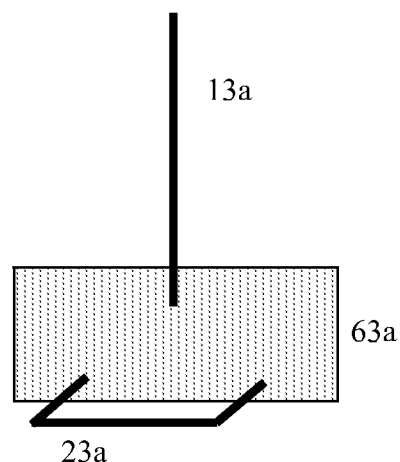
FIG. 3 in two sub-figures, examples of how the antenna arrays can be mechanically combined with an electronic circuit of the patient device according to the invention, structured as a circuit board.
Figure 3:
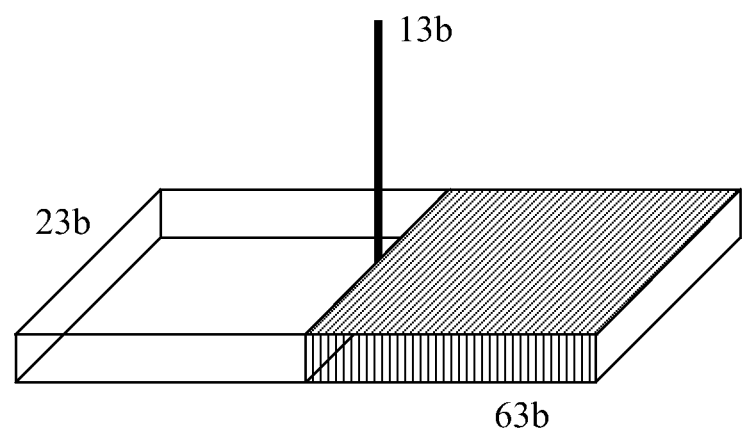

FIG. 3 shows, in two sub-figures, how the antenna arrays can be combined with an electronic circuit of the patient device according to the invention, structured as a circuit board. In the first partial figure, an E-field antenna 13a is attached at the center of an edge of a circuit board 63a, on which the electronic circuit of the transmitter/receiver device as well as any other components such as adaptation networks and the like are applied, so that the main axis of the E-field antenna 13a is oriented at least approximately parallel to a plane described by the circuit board 63a. A frame antenna 23a is attached in the lower region of the circuit board 63a, perpendicular to its two surfaces. The frame antenna 23a is made from a rigid conductive material, so that no additional mechanical stabilization is required. The feed points of both the E-field antenna 13a and of the frame antenna 23a lie on the circuit board, so that particularly simple connection with the electronic circuits of the transmitter/receiver device is possible. As was already the case above, the main axis of the E-field antenna 13a is oriented at least approximately parallel to a normal line of an area covered by the frame antenna 23a.

In the exemplary embodiment shown in the second partial figure, the E-field antenna 13b is disposed perpendicular to the circuit board 63b. The frame antenna 23b lies in a plane with the circuit board 63b, and encloses this in one half of the frame antenna 23b. Here again, the E-field antenna 13b is disposed at least approximately parallel to an area normal line of the area covered by the frame antenna 23b. Again, the feed points of the two antennas lie on the circuit board 63b.

Figure 4:
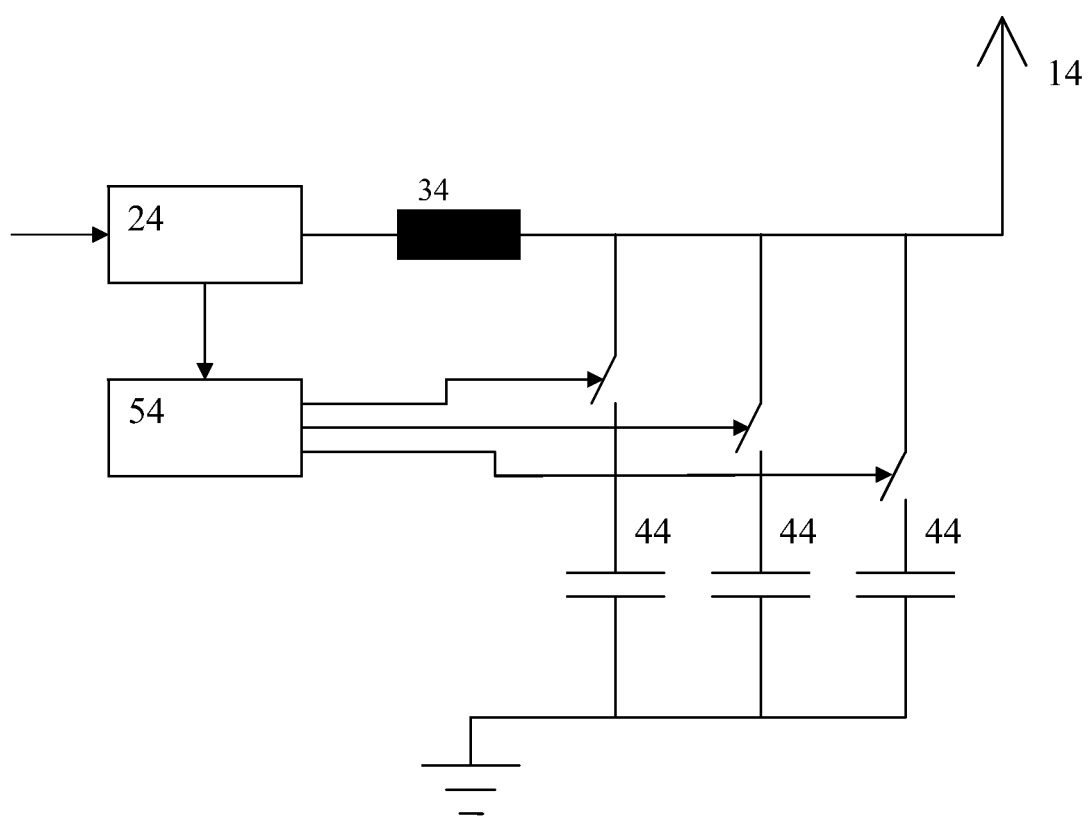
FIG. 4 a first variant of an adaptation network.

FIG. 4 shows a first variant of an adaptation network. The circuit example only shows an adaptation network for an E-field antenna 14, which is electrically lengthened by the inductance 34 switched between the E-field antenna 14 and the directional coupler 24. Other antennas, such as, in particular, an H-field antenna, can be connected with the transmitter/receiver device to which the E-field antenna 14 is connected by way of the directional coupler 24. In order to make adaptation of the E-field antenna 14 changeable, and thus to be able to adapt the E-field antenna 14 to changing emission and reception conditions, three capacitors 44 are disposed between the antenna line and ground, in switchable manner, in the example. In this connection, the capacitors 44 are structured so that they can be connected with the antenna line by way of switches, preferably transistors. A controller 54 receives a signal from the directional coupler 24, which signal represents a measure of the adaptation of the antenna, particularly in the transmission case. The controller 54 strives to minimize the (power) signal received from the directional coupler 24, or to lower it below a predetermined amount, in that it changes the antenna adaptation dynamically, by way of suitable switching signals for the switches disposed on the capacitors 44. Of course, the exemplary embodiment is not restricted to a number of three capacitors 44. It is advantageous if the capacitors 44 demonstrate capacitance values that increase in binary manner, so that the greatest possible number of different capacitance values can be combined from a minimal number of capacitors 44.

Figure 5:
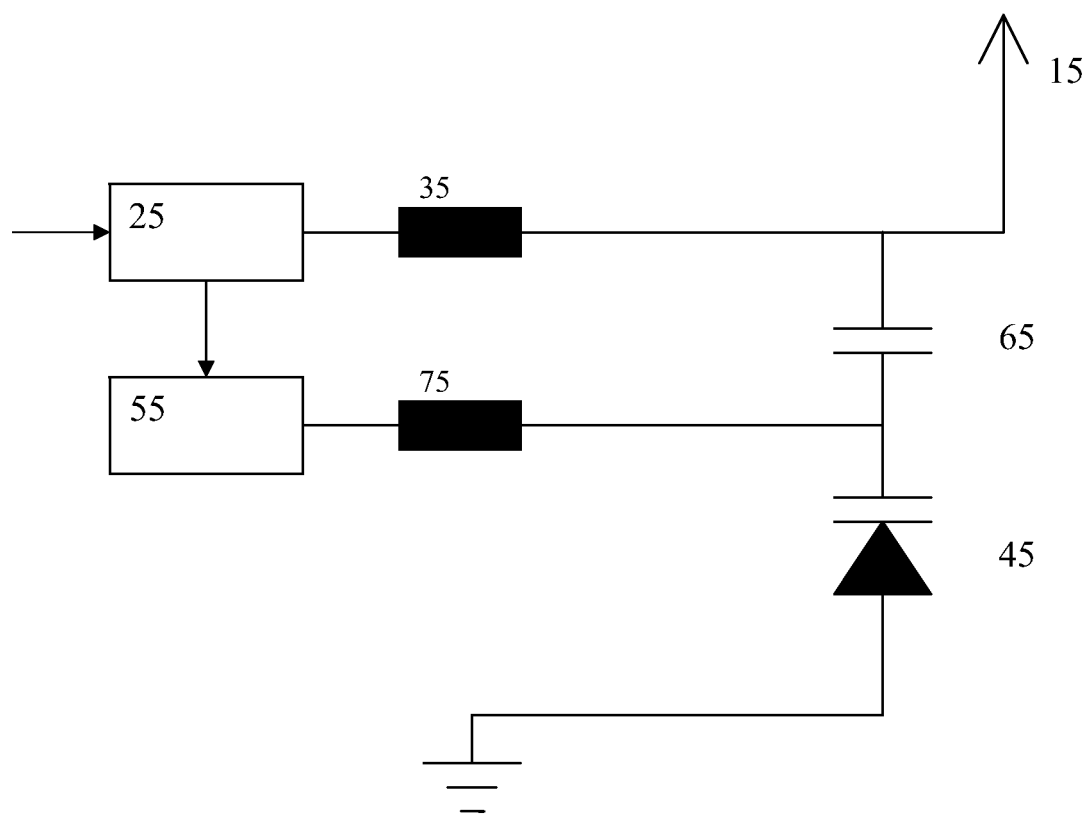
FIG. 5 a second variant of an adaptation network.

FIG. 5 shows a second variant of an adaptation network. The second exemplary embodiment differs from the first in the manner in which the variable capacitance for adaptation is implemented. Fundamentally, it is also possible to combine the two variants with one another. The adaptation network of the second variant comprises a varactor diode 45, which is switched between ground and a capacitor 65 in the cut-off direction. A second connector of the capacitor 65 is connected with the antenna line. The varactor diode 45 has a variable capacitance that depends on the amount of the cut-off voltage by way of the varactor diode 45. The cut-off voltage, and thus the adaptation of the antenna, is set by the controller 55 as a function of the signal made available by the directional coupler 25, which signal represents a measure of the adaptation of the antenna. The changeable cut-off voltage brings about a change in the capacitance of the varactor diode. The second inductance 75 serves to uncouple the high-frequency transmission or reception signal, respectively, from the direct voltage source disposed in the controller, which generates the cut-off voltage.

Figure 6:
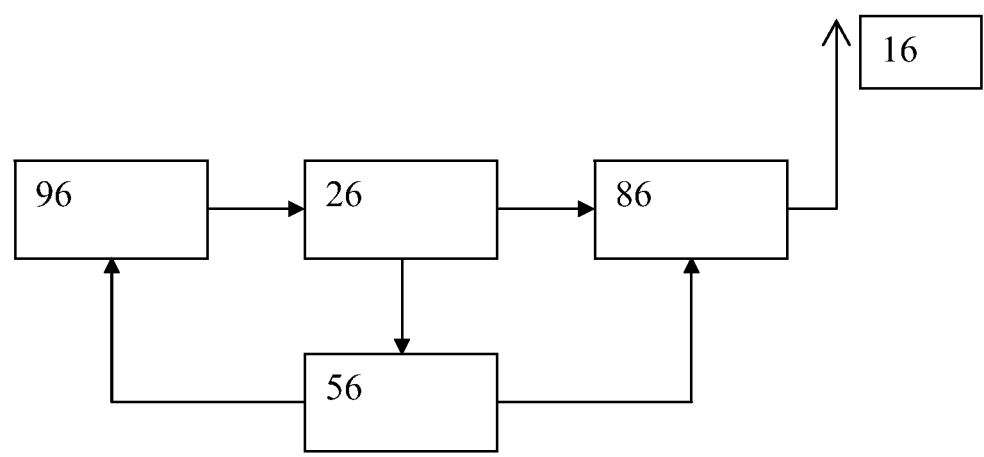
FIG. 6 a block schematic of a transmitter/receiver device with adaptation network.

FIG. 6 shows a block schematic of a transmitter/receiver device having an adaptation network. The transmitter/receiver device comprises an RF circuit 96, which contains a power amplifier to generate the transmission signal, among other things. The transmitter/receiver device is preferably switchable between a transmitting and a receiving mode, in half-duplex operation. Accordingly, the RF-circuit 96 also comprises switching components required for reception, such as a low-noise amplifier and the like. The transmission signal of the RF-circuit 96 is given to the adaptation network 86 by way of a measurement circuit 26, which is preferably structured as a directional coupler. At the same time, the measurement circuit 26 generates a measurement signal for the controller 56, which determines, using the measurement signal, how well the antenna 16 connected with the adaptation network 86 is adapted. The controller 56 generates suitable control signals for the RF-circuit 96 and the adaptation network 86, in order to change the adaptation of the antenna in such a manner that the adaptation is optimized or brought to a specific value.

What is claimed is:

1. A patient device comprising:
    at least one E-field antenna;
    an H-field antenna;
    a transmitter/receiver device coupled with the at least one E-field antenna and the H-field antenna;
    a planar circuit board;
    wherein the H-field antenna is structured as a frame antenna, wherein a main axis of the at least one E-field antenna forms an angle of less than 30 degrees to a normal line of an area generated by the frame antenna;
    wherein the at least one E-field antenna is attached at the center of an edge of a circuit board and the frame antenna is attached in a lower region of the circuit board perpendicular to the two surfaces of the circuit board, wherein the frame antenna is made from a rigid conductive material;
    a controller;
    a tunable adaptation network that can be tuned by the controller; and,
    wherein the tunable adaptation network comprises
        at least three capacitors having capacitance values that increase in binary values with respect to one another wherein the at least three capacitors are configured to be switched in parallel to provide an antenna capacitance,
        a varactor diode coupled with said the at least one E-field antenna and the H-field antenna wherein said varactor diode is configured to fine tune said antenna capacitance,
        wherein the controller is configured to connect one or more of the at least three capacitors with at least one of the at least one E-field antenna and the H-field antenna, and to electrically insulate remaining capacitors from at least one of the at least one E-field antenna and the H-field antenna.

2. The patient device according to claim 1, in which the main axis is parallel to the normal line.

3. The patient device according to claim 1, in which the main axis runs through the area generated by the frame antenna.

4. The patient device according to claim 1, in which the at least one E-field antenna is electrically lengthened.

5. The patient device according to claim 1, in which the H-field antenna is electrically lengthened.

6. The patient device according to claim 1, in which the at least one E-field antenna is structured as a rod antenna or a helical antenna.

7. The patient device according to claim 1, wherein the at least one E-field antenna and the H-field antenna comprise a resonance frequency between 300 MHz and 500 MHz, and can operate in a range between 300 MHz and 500 MHz.

8. The patient device according to claim 1, wherein the at least one E-field antenna is structured as a quarter-wave dipole with an antenna counterweight.

9. The patient device according to claim 1, wherein the transmitter/receiver device of the patient device is configured to select either the at least one E-field antenna or the H-field antenna for reception, as a function of a reception strength of a received signal.

10. The patient device according to claim 1, in which at least one of the at least one E-field antenna and the H-field antenna is connected with the transmitter/receiver device by way of a directional coupler, wherein the directional coupler is configured to output a measurement signal to the controller, and the measurement signal indicates a measure for a power reflected or received by at least one of the at least one E-field antenna and the H-field antenna.

11. The patient device according to claim 1, wherein the transmitter/receiver device of the patient device is configured to sum up signals of said at least one E-field antenna and said H-field antenna.

* * * * *